United States Patent [19]

Eikman

[11] Patent Number: 4,590,158
[45] Date of Patent: May 20, 1986

[54] MICROBIAL MONITOR

[76] Inventor: Edward A. Eikman, 5116 Longfellow Ave., Tampa, Fla. 33609

[21] Appl. No.: 299,614

[22] Filed: Sep. 4, 1981

Related U.S. Application Data

[63] Continuation-in-part of Ser. No. 80,327, Oct. 1, 1979, abandoned.

[51] Int. Cl.[4] ............................................. C12Q 1/24
[52] U.S. Cl. ........................................ 435/34; 435/29; 435/35; 435/39; 435/290; 435/291; 435/293; 435/294
[58] Field of Search ........................... 23/230 B, 230.3; 128/760, 762; 422/63, 66, 71; 424/1, 1.5; 435/29, 34, 35, 39, 287, 289, 290–294

[56] References Cited

U.S. PATENT DOCUMENTS

| | | | |
|---|---|---|---|
| 3,129,144 | 4/1964 | Page et al. | 435/291 |
| 3,817,239 | 6/1974 | Kuntz | 128/762 |
| 3,844,894 | 10/1974 | Kronick et al. | 435/291 |
| 3,935,073 | 1/1976 | Waters | 435/35 |
| 3,952,729 | 4/1976 | Libman et al. | 128/762 |
| 3,956,070 | 5/1976 | Kenyon | 435/30 |
| 3,969,496 | 7/1976 | Schrot | 435/35 |
| 3,997,404 | 12/1976 | Waters | 435/35 |
| 4,021,308 | 5/1977 | Saxholm | 435/291 |
| 4,057,470 | 11/1977 | Schrot | 435/35 |
| 4,071,315 | 1/1978 | Chateau | 435/291 |
| 4,197,369 | 4/1980 | Weaver | 435/29 |
| 4,272,482 | 6/1981 | Jessop et al. | 422/66 |

Primary Examiner—Peter Hruskoci
Attorney, Agent, or Firm—Lane and Aitken

[57] ABSTRACT

In a system for monitoring fluid for microbial contamination, successive samples of the fluid to be monitored are aseptically directed periodically to a growth medium. A detector detects gaseous metabolic products evolving from the growth medium to provide an indication of incipient contamination of the fluid being monitored.

19 Claims, 21 Drawing Figures

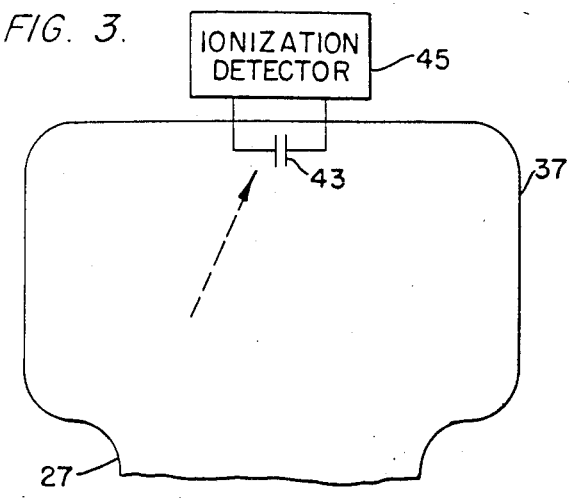
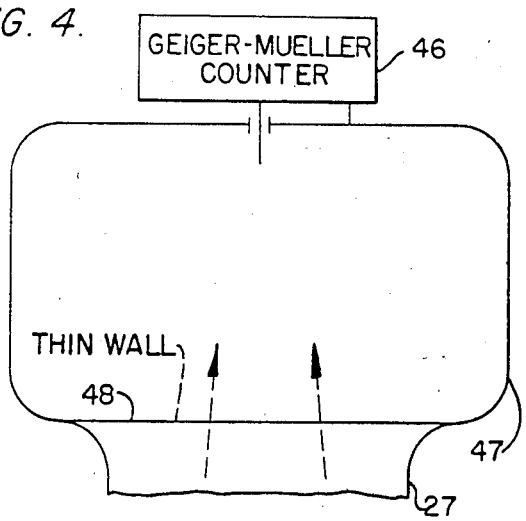
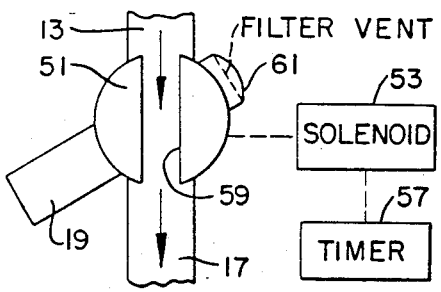
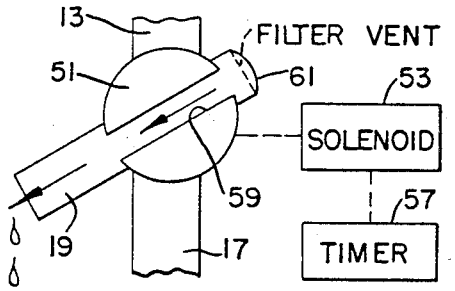
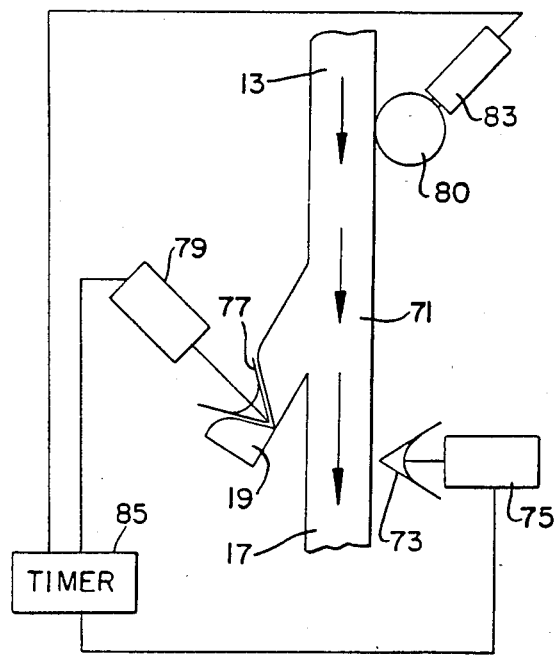
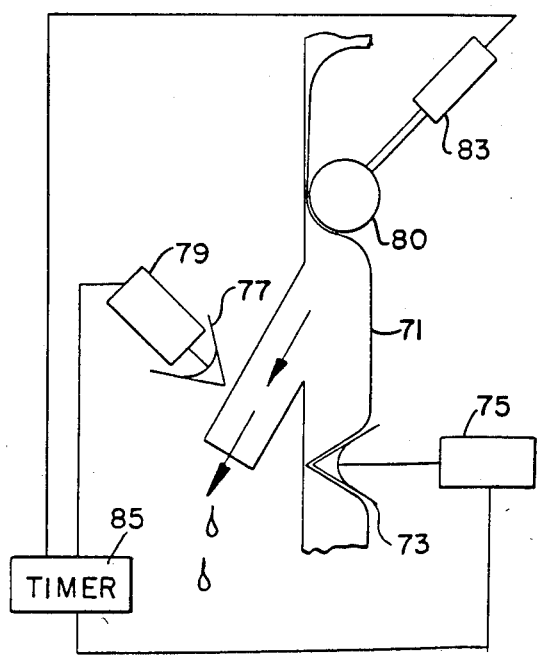

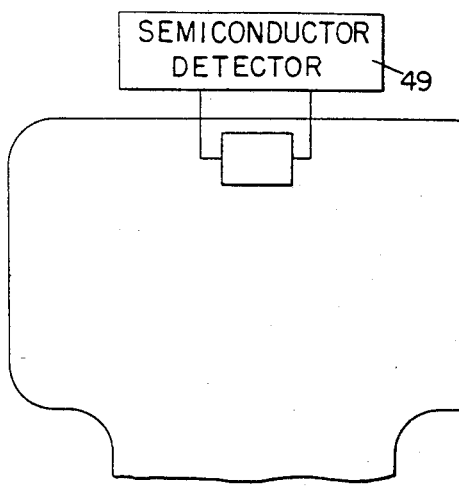
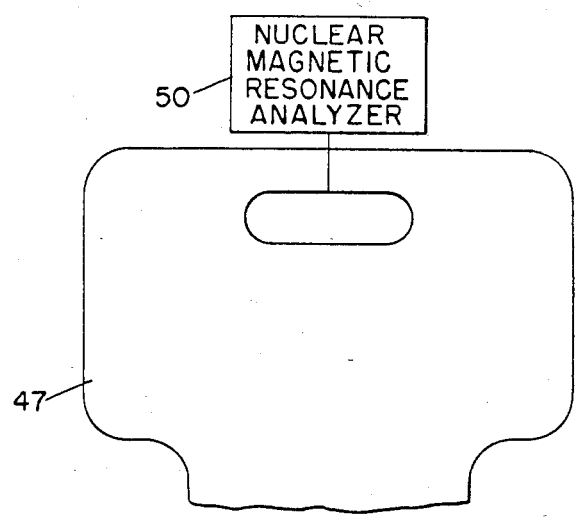
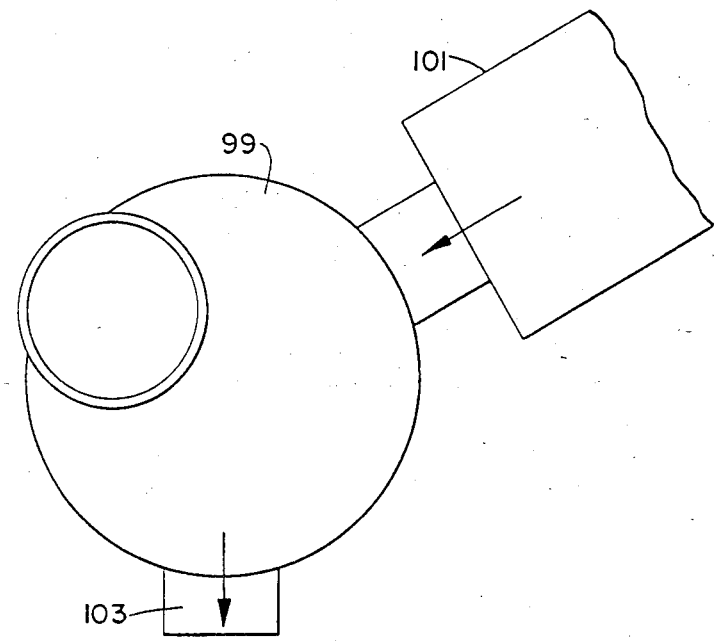
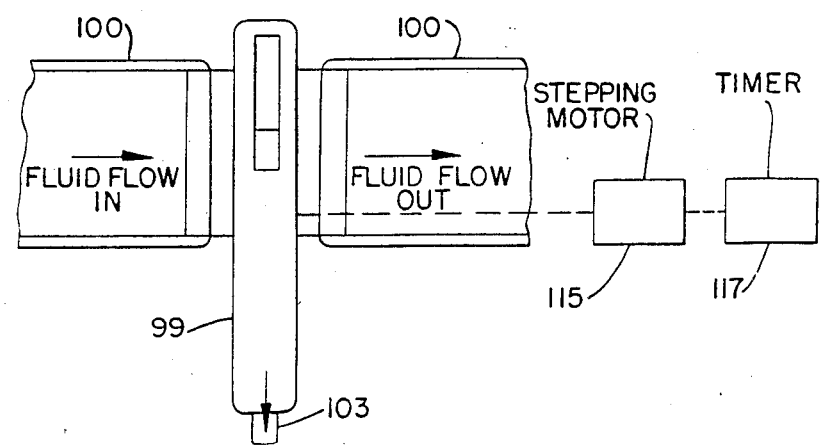

MICROBIAL MONITOR

This application is a continuation in part of application Ser. No. 80,327 filed Oct. 1, 1979 now abandoned.

BACKGROUND OF THE INVENTION

This invention relates to a system for monitoring fluids for microbial contamination and, more particularly, to such system designed to automatically sample potentially contaminatable fluid and indicate when contamination of such fluid occurs.

The invention is particularly useful for detecting contamination of urine in catheterized patients, who are susceptible to infection of the urinary tract resulting in contamination of the urine. Prior to the present invention, contamination of urine in catheterized patients was monitored by periodically collecting individual urine samples and culturing each sample to determine the presence of contamination. Because each urine sample had to be sent to a laboratory to be individually cultured and because of the expense of collecting and processing frequent individual cultures resulting in an average time delay before the collection of the first sample of urine after contamination appears in the urine, a substantial amount of time would normally elapse between the time of contamination appearing in the urine and the time of determining that the urine was contaminated. As a result, by the time it had been determined that the urine was contaminated, the patient often already had a massive infection. Moreover, each separate sample collection was subject to accidental contamination, leading to occasional false positive cultures.

The present invention overcomes these problems of the prior art technique by providing a much earlier indication of the presence of contamination. This is achieved by providing at the site of a patient a liquid culture medium and periodic urine samples are automatically fed into the same tracer-labeled culture medium over an extended time interval. The cost of using the system does not vary with the number of samples collected and, accordingly, the frequency of sampling is based solely upon medical requirements, without regard to the cost of the additional samples. As soon as contamination of the urine begins, the first sample containing contamination will be aseptically collected and incubation will begin instantaneously in the growth medium. As a result, the growth medium will evolve gas, which will be detected by a detector to provide an early indication of the presence of such gas thus indicating the presence of microbial contamination in the urine. The system differs from the prior art systems, not only in the automatic sampling of the urine from the patient, but also in the fact that each urine sample is aseptically diverted into the same culture medium as the previous samples. Each urine sample can be fed into the same culture medium because the system is designed only to detect the presence of contamination and the samples of urine taken from the patient prior to infection of the patient would be sterile and would not effect the ability of the culture medium to respond to a later contaminated sample.

It will be evident that the system as described is also applicable to detect the presence of contamination in other fluids by automatically taking periodic samples of the fluids including fluids from wound drainage, dialysis fluids, peritoneal cavity drainage, cerebro-spinal fluid drainage, exhaled air, fluids undergoing or intended for intravenous administration or inhalation, fluids in industrial processes including food preparations, particles of solids or liquids within fluid streams, or any normally sterile or culturable fluid. It likewise will be evident that any convenient means of detecting microbial growth may be used in the system.

BRIEF DESCRIPTION OF THE DRAWINGS

FIG. 3 is a schematic illustration of another embodiment of the radioactive gas detector employing an ionization chamber;

FIG. 4 is a schematic illustration of yet another embodiment of the radioactive gas detector employing a Geiger-Mueller counter;

FIG. 5 is a schematic illustration of another embodiment of the radioactive gas detector employing a semiconductor radioactivity detector;

FIG. 6 is a schematic illustration of another embodiment of the system using a nuclear magnetic resonance analyzer to detect change in the nuclide contends of the gas mixture composition due to the evolution of metabolic products;

FIGS. 7 and 8 schematically illustrate the two operable positions of one embodiment of the sampler of the system in FIG. 1; and FIGS. 9 and 10 schematically illustrate the two operative positions of another embodiment of the sampler of FIG. 1;

FIGS. 11-16 are schematic illustrations of another embodiment of the sampler in FIG. 1, with provision for continuous sampling and concentration of the sample; and FIGS. 17-21 are schematic illustrations of another embodiment of the sampler in FIG. 1, with provision for continuous sampling and concentration of the sample.

DESCRIPTION OF THE PREFERRED EMBODIMENTS

Figure 1:
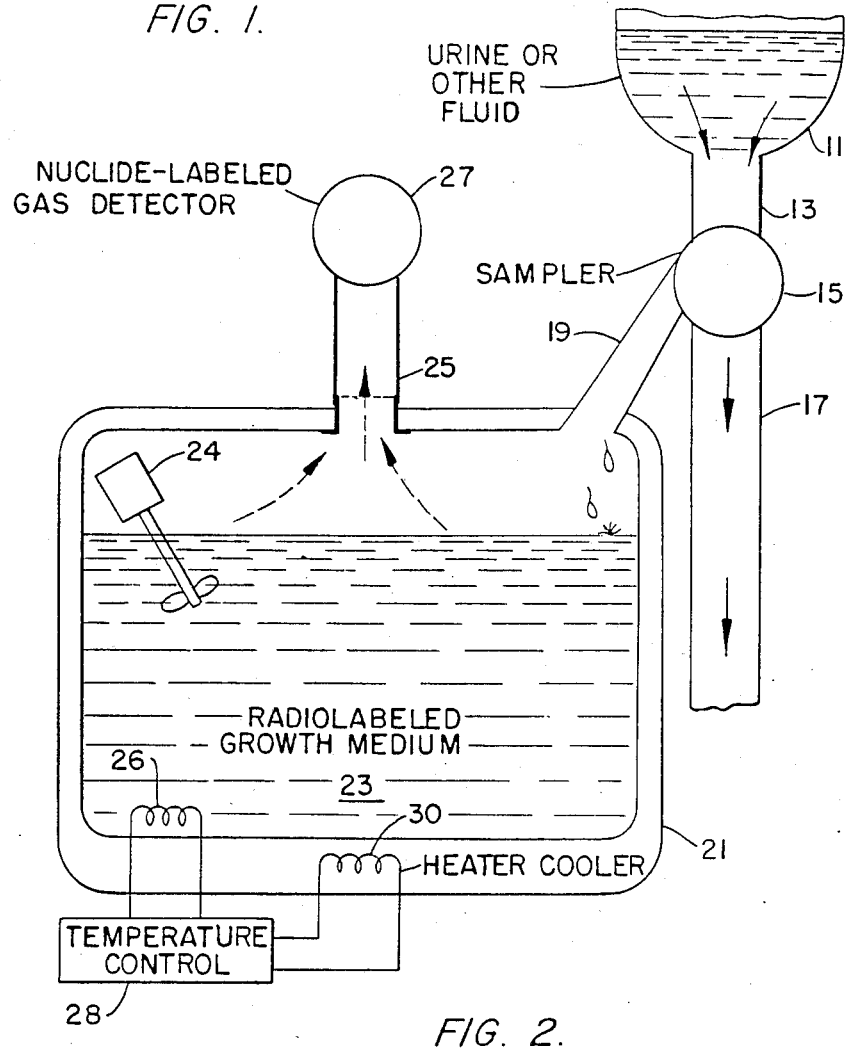
FIG. 1 is a schematic diagram illustrating the system of the present invention.

As shown in FIG. 1, the liquid, such as urine, being monitored from a source 11 flows through tubing 13 to an intermittent sampler 15. Fluid normally exits from the intermittent sampler 15 through tubing 17 to a suitable collector or waste disposal system, not shown. Periodically, at regular intervals, the sampler 15 directs a small sample from the fluid automatically through tubing 19 into a container 21, which contains a suitable tracer labeled liquid growth or culture medium 23. For catheterized patients, the sampling rate of urine samples should be in the range of once every ten minutes to once every hour. For industrial applications, the sampling rate may be once every six hours, or very small samples may be taken at more frequent intervals.

The container 21 has an insulating jacket and is provided with a suitable agitator 24 to stir the growth medium. A thermostat 26 senses the temperature within the growth medium 23 and signals a temperature control 28, which operates a heater-cooler 30 to maintain the temperature within the medium 23 to promote the growth of micro-organisms. This temperature will usually be selected to be 37° C.

The growth medium 23 contains one or more tracer-labeled nutritional substrates, which produce tracer-containing gaseous products when metabolized. The composition of the medium is selected to favor the growth of categories or types of organisms of greatest importance or interest and inhibit the growth of other types of organisms. The composition of the medium allows evolution of the appropriate gaseous products rather than retention of the products in solution. For example, the pH of the solution may be selected to release carbon dioxide. The culture medium is of sufficiently large volume so that the successive samples introduced into the medium through the tubing 19 have no substantial effect on the characteristics of the growth medium over a substantial period of time and for a substantial number of samples.

The space in the container 21 over the growth medium 23 communicates through an exit port 18 and a conduit 25 with a gas detector 27. The top of the exit port is closed by a gas permeable membrane 20. When the growth medium 23 evolves tracer containing gas, some of this gas will pass through the gas permeable membrane and the conduit 25 into the detector 27 and be detected thereby thus indicating the presence of micro-organisms in the sample introduced into the growth medium and, accordingly, indicating contamination of the fluid being monitored. The conduit 25 fits with the exit port 18 in a manner so that the container 21 together with membrane 20 can be removed and replaced with another container containing a fresh growth medium. The purpose of the membrane 20 is to exclude the substances of the growth medium from the detector 27 and to prevent extraneous contaminating substances from entering the container 21 and the growth medium 23 while permitting the transmission of tracer containing gaseous substances for detection.

Figure 2:
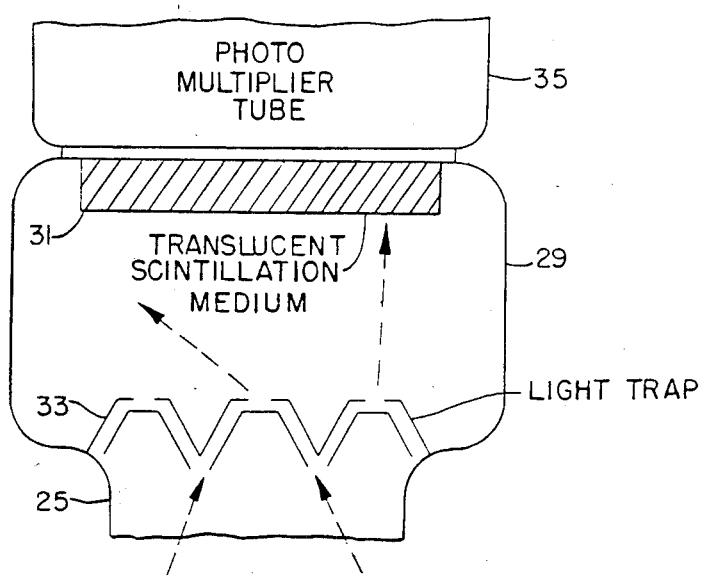
FIG. 2 is a schematic illustration of an embodiment of the radioactive gas detector of the scintillation type for use in the system of FIG. 1.

FIG. 2 schematically illustrates an example of radioactive gas detector which may be used in the system of FIG. 1. Nutritional substrates in growth medium 23 include radionuclides emitting radioactivity of sufficiently low penetration that little radioactivity reaches the radioactivity detector unless a radioactive gas is produced by metabolism of the nutritional substrates. As shown in FIG. 2, the detector comprises a chamber 29 having a translucent scintillation medium 31, such as an activated sodium iodide crystal radiation detector contained in a thin, gas-tight envelope, positioned at the top thereof.

A preferred embodiment uses as scintillation medium 31 a translucent substrate using an organic scintillation medium such as "Liquifluor", commercially available from the New England Nuclear Company. The translucent substrate may contain, in addition to a scintillation medium, an alkaline substance, such as the residue from the addition of an aqueous solution of 0.1N KOH, in order to favor the accumulation of gaseous carbon dioxide, thereby bringing the radioactive gas in close proximity to the scintillation medium 31. A light trap 33 is provided across the mouth of the chamber 29 which communicates with the conduit 25, the light trap permitting gas to flow into the chamber 29. When the radio emission from the radioactive gases impinges upon the scintillation medium 31, it will emit light scintillations, which, in turn, will be detected by a photomultiplier tube 35. The light trap 33 prevents ambient light from causing false indications due to photoactivation whenever light is admitted, for example, in the process of renewing the growth medium 23.

In this embodiment of the system, the photomultiplier tube is protected from ambient or fluorescent light from sources other than scintillations induced by radioactive gases in the chamber 29. This protection is accomplished by the use of opaque construction materials and coatings to exclude ambient light from the system.

Alternatively, the detector 27, as shown in FIG. 3, may comprise an ionization chamber 37. The ionization chamber 37 contains electrodes 43 of an ionization detector 45. When radioactive gas passes into the chamber 37, it will cause ionization of the gases in the chamber 37. This ionization will be detected by the ionization detector 45, which will then provide an indication that the fluid being monitored has become contaminated.

A third embodiment of the radio gas detector is illustrated in FIG. 4 which employs a Geiger-Mueller counter to detect the presence of radioactive gases in a chamber 47. In this embodiment, the chamber 47 communicates with the conduit 27 through a thin wall 48. This wall is sufficiently thin to admit emissions from the radioactivity 8/17/81 in conduit 25.

A fourth embodiment is illustrated in FIG. 5, in which a semiconductor radioactivity detector 49 is used to detect the presence of radioactive gases in chamber 47.

Another embodiment of the invention is illustrated in FIG. 6, in which a nuclear magnetic resonance analyzer 50 is used to detect change in the nuclide contents of the gas mixture in chamber 47. This embodiment is particularly useful for the detection of the evolution of gases containing stable nuclides as evidence of contamination in the liquid growth medium. In this embodiment, the application of the invention is realized without the use of radioactive nuclides that may result in hazards associated with their use or disposal. For example, gaseous Carbon-13 dioxide may be detected as a product of the metabolism by contaminating micro-organisms. In each of the embodiments of the gas detector 27 shown in FIGS. 3-6, means may be employed to increase the concentration of gases to be detected. For example, in the embodiment of FIG. 4, a thin layer of alkali may be added to the side of the thin wall 48 that faces the conduit 25 to aid in the accumulation of carbon dioxide at the thin wall 48, thereby increasing the likelihood that radioactive carbon dioxide is detected.

The gas detection apparatus used in any of these embodiments is provided with an audible alarm, not shown, or other signaling device in order to alert interested personnel to the presence of signs of contamination when detected. In an analogous manner, other changes in the properties of growth media that occur as a result of microbial growth may be used to detect contamination.

As shown in FIGS. 7 and 8, the intermittent sampler 15 may comprise a rotary valve 51 operated by a solenoid 53 controlled in turn by a timer 57. The rotary valve 51 comprises a passageway 59 which, in the position shown in FIG. 7, directs the fluid from the tube 13 to the tube 17. By means of the solenoid 53, the valve 51 can be moved to the position shown in FIG. 8 in which it connects between the tube 19 and a vent 61 closed by a filter. At regular intervals, the timer 57 will energize the solenoid 53, which in turn will actuate the valve 51 to the position shown in FIG. 8 momentarily and then return it to the position shown in FIG. 7. When the valve is actuated to the position shown in FIG. 8, the sample of fluid contained in the conduit 59 will be directed into the chamber 21 through the tube 19.

In the embodiment of intermittent sampler 15 shown in FIGS. 9 and 10, the tube 19 and the tubes 13 and 15 are implemented by flexible tubing with the tube 19 and 17 joining the tube 13 in the Y-connection 71. A stop clamp 73 operated by a solenoid 75 is provided to selectively close the tube 17 just below the Y-connection 71. A stop clamp 77 operated by a solenoid 79 is provided to selectively close the tube 19 just below the Y-connection 71. A roller 80 operated by a solenoid 83 is provided to selectively close and flush the tube 13 above the Y-connector 17 as shown in FIG. 10. The solenoids 75, 77 and 83 are controlled by a timer 85. In their normal positions, the solenoids will be de-energized in which case the clamp 77 will close the tube 19, the clamp 73 will leave the tube 17 open and the clamp 80 will leave the tube 13 open as illustrated in FIG. 9. At periodic intervals, the timer energizes the solenoids 75, 77, and 83 to cause the clamp 73 to momentarily close the tube 17, the clamp 77 to momentarily open the tube 19, and the roller 80 to momentarily close the tube 13 so that a small sample of fluid of limited volume may flow through the tube 19 into the chamber 21. When the solenoid 83 is energized to actuate the roller 80, the roller 80 not only closes the tube 13, but also, as shown in FIG. 10, moves along a short portion of the tube 13 toward the Y-connector 17 to flush fluid in the tube 13 through the tube 19 into the chamber 21. The device represented by the roller 80 and the flexible tube 13 is referred to as a peristalic pump. A moment after the flushing of the fluid by roller 80, the solenoids 75, 77 and 83 are de-energized and the clamps 73 and 75 return to the position shown in FIG. 9 and the roller 80 returns to the position shown in FIG. 9.

It will be observed that with both the embodiments of the intermittent sampler, the sample that is intermittently directed into the chamber 21 is controlled in volume so that only a few drops may flow into the chamber 21 at the time of taking of each sample. With the embodiments of FIGS. 9 and 10, it is limited to the amount contained above the clamp 77 and below the clamp 80. The size of the periodic sample is limited to be a small amount in this way so as not to have a significant effect upon the desirable characteristics of the growth medium. Typically, the volume of each sample is about 0.1 milliliters and should not exceed 1 milliliter. The growth medium perferably has a volume on the order of 100 times the volume of the samples and at a minimum, should be at least 10 times the volume of the samples.

Whenever contamination in the fluid is intermittent or in low concentration, it is necessary that sampler concentrate material from the fluid flow to be monitored. FIGS. 11-21 illustrate two preferred embodiments of the sampler that concentrates material from the fluid flow. In these embodiments, components from the fluid stream that are suspected to be associated with contamination are collected nearly continuously in order to increase the liklihood of early detection of contamination. The collected components are then introduced into the growth medium at selected intervals.

In the embodiments illustrated in FIGS. 11 through 15, a sampler 99 is provided to successively and periodically transport porous collection discs into a stream being monitored and then deliver the discs to the growth medium. FIG. 11 schematically illustrates the apparatus viewed in elevation in the direction of the flow of the fluid being monitored to the sampler 99 and FIG. 12 illustrates the apparatus viewed perpendicularly to the direction of fluid flow. As shown in FIG. 11, the sampler 99 is provided with suitable means 101 of supplying fresh discs for collecting samples to the sampler 99 and with a suitable passageway 103 to deliver discs to the chamber containing the liquid growth medium. As shown in FIG. 11, the sampler 99 is connected in tubing 100 containing the flowing fluid that is to be monitored. In FIG. 11, the apparatus is illustrated without the tubing 100 connected.

Figure 13:
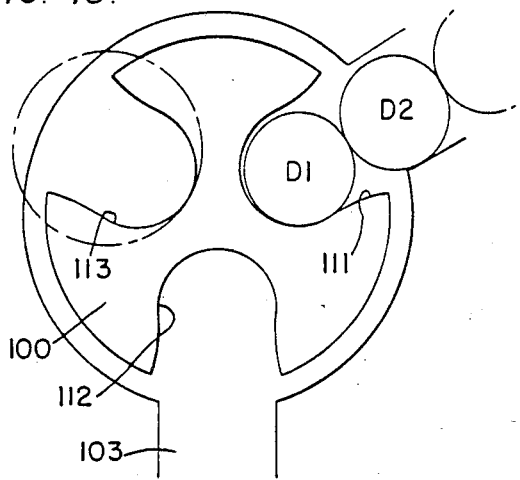
Figure 14:
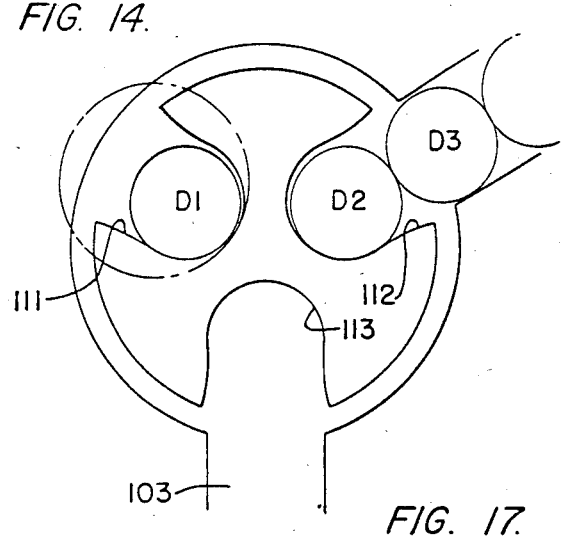
Figure 15:
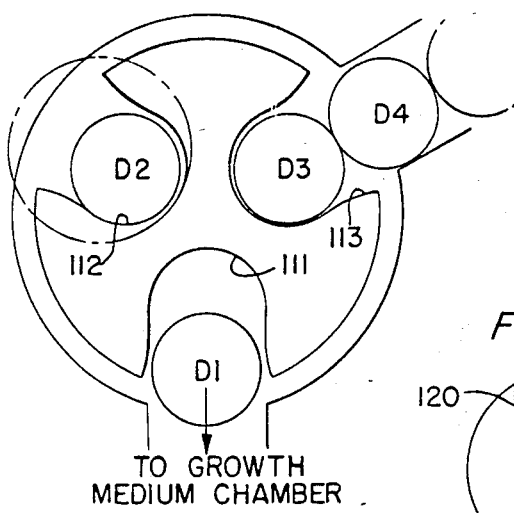

FIGS. 13, 14 and 15 illustrate a cutaway view of the sampler 99 and, as shown in these figures, the sampler 99 contains a turntable 105, in the edges of which are defined three disc receiving pockets 111-113. FIGS. 13, 14 and 15 illustrate the turntable 105 in the sampler 99 in each of three rest positions. In the rest position shown in FIG. 13, a collection disc D1 from the supply means 105 falls into the pocket 111 in the turntable 105. The turntable 105 is rotated counterclockwise in 120° increments at predetermined intervals by means of a stepping motor 115 controlled by a timer 117 as shown in FIG. 12. The sequence of rotation of the turntable is from the rest position of FIG. 13 to the rest position of FIG. 14 and then to the rest position of FIG. 15. In the rest position of FIG. 14, the disc D1 is introduced into the fluid stream flowing from the tubing 100 to the sampler 99 and a fresh disc D2 is allowed to enter pocket 112 in the turntable 105.

The turntable rotates after a specified collection interval to the position shown in FIG. 15. This brings fresh disc D2 into collection position, drops the disc D1 that previously occupied the collection position into the growth medium 23 for culture, and allows another fresh disc D3 to enter pocket 113 in the turntable.

Figure 16:
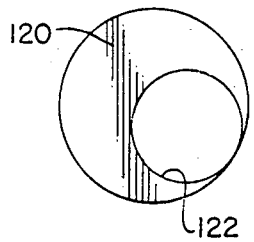

Each time a disc is brought into the collection position, fluid from the tubing 100 comes in contact with the disc when it is positioned in the flow of the fluid and is allowed to flow around it so that the disc collects material from the fluid flow by adsorption and/or by filtration. Alternatively, as shown in FIG. 16, a baffle 120 may be provided in the sampler 99 in the flow path of the fluid with the baffle containing an aperture 122 aligned with and corresponding in size to the size of the discs so that the baffle directs substantially all of the fluid to flow through a disc when it is positioned in the fluid stream. In this embodiment, the disc collects material from the fluid flow by filtration.

The turntable continues to rotate in 120° increments at specified intervals, adding a collection disc to the incubation medium with each incremental rotation. The discs are sufficiently small in relation to the volume of the incubation medium so that the circulation of the medium remains sufficient for growth purposes after a large number of discs have been added. In some cases, the disc may be so constructed that after immersion in the growth medium for a period of time equal to several of the specified sampling intervals, the disc disintegrates into many particles when the growth medium is agitated. This subdivision of the disc reduces any tendency of the discs to prevent free circulation of growth medium.

Figure 17:
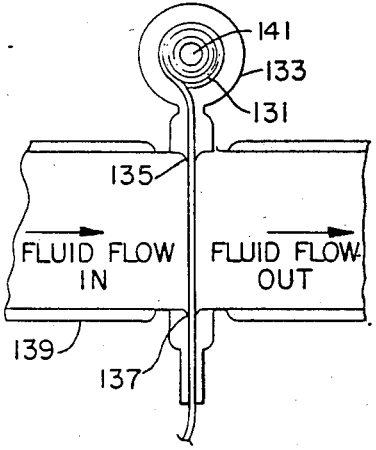
Figure 18:
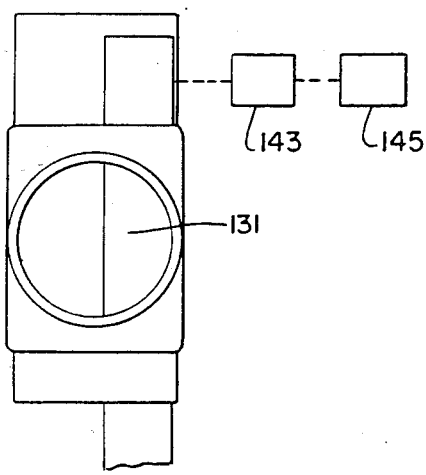
Figure 19:
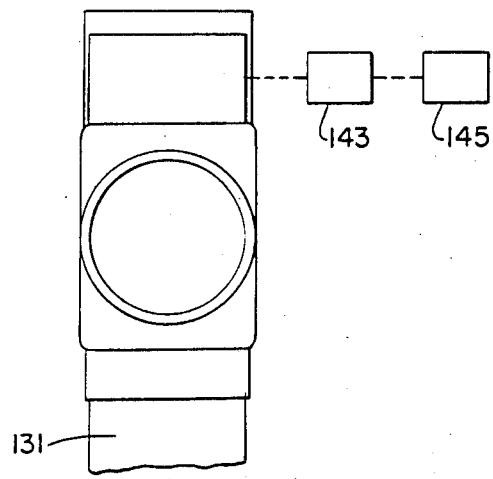

In the embodiments of the invention shown in FIGS. 17-19, a coil of fresh sample strip 131 is wound in a container 133. FIG. 17 schematically illustrates the apparatus viewed perpendicularly to the direction of flow of the fluid being monitored. FIGS. 18 and 19 each illustrate an alternative arrangement of the apparatus viewed in the direction of the flow of fluid. As shown in FIG. 17, the end of the sample strip is threaded through an entrance slot 135 and an exit slot 137 in the sidewall of tubing 139 so that the sample strip passes through the interior of the tubing 139 to come into contact with the fluid flowing through the tubing 139. The sample strip is wound on an axle 141 which is driven by a stepping motor 143 under the control of a timer 145 (see FIGS. 18 and 19). The stepping motor 143 incrementally advances the sample strip to the tubing 139 and the sample strip collects material from the fluid flow by adsorption and filtration. A particular problem arises when fluid that is being sampled may itself inhibit microbial growth. For example, a patient on drug treatment may at times excrete substantial amounts of drugs in the urine that could inhibit microbial growth. The presence of such a material may substantially slow growth in growth media, and delay or prevent the detection of contamination. In such a case, the sample strip may go through an additional stage of rinsing or neutralization to remove such materials, while retaining microbes accumulated through filtration or adsorption. From the exit slit 137, the strip with the collected samples is fed to the growth medium where the sample is incumbated and contamination detected as described above.

Instead of incrementally advancing of the sample strip by driving the axle on which the sample strip is wound, the strip may be advanced incrementally by pinch rollers pulling the strip through the exit slot 37.

As shown in FIG. 18, the strip may just occupy part of the tubing allowing for part of the fluid to bypass the sample strip or the strip may be arranged to completely fill the cross-section of the tubing, as shown in FIG. 20, so that all of the fluid flow flows through the sample strip.

In the embodiments described above, when sufficient uncontaminated samples have been introduced into the growth medium that they would begin to have a significant effect on the growth medium, the growth medium is replaced with a fresh growth medium. For this reason, the chamber containing the growth medium is made disposable, and a fresh growth medium is provided simply by replacing the chamber 21 with a new chamber containing the fresh medium. Part or all of the sampling mechanism is detached with the chamber in order to maintain the sterility of the growth medium for further testing or processing. The growth medium may be sampled for terminal culture, or independent culture, at any time by means of a sterile needle introduced through the wall of the chamber, or any convenient entry port. As stated above, a function of membrane 20 is to protect growth media 23 from contamination. The membrane is permanently attached to container 21, and changed along with the container when it is desired to replace the growth media. A hydrophobic plastic filter with a pore size of 0.01 micron is an example of a membrane that selectively excludes particulate contamination such as bacteria, and excludes liquid growth media, but which permits the passage of gaseous carbon dioxide. When desired or between changes of growth media, the alkali, applied to the scintillation medium in the embodiment of FIG. 2 and to the thin wall 48 in the embodiment of FIG. 4, may be replaced or purged of any radioactive substances or other accumulations by rinsing with a solution that will dissolve accumulated substances. An excess of alkaline solution is an example of such a rinse solution for removal of carbon dioxide. Preferably the period at which the growth medium is replaced is selected to be short enough that the total volume of the samples introduced into the growth medium does not exceed 25 percent of the volume of the growth medium. The growth medium would normally be replaced once every day or two, or in special circumstances, at longer intervals. From the standpoint of practicality, the growth medium would not be replaced at intervals of less than one hour. Accordingly, the sampling means operates to periodically introduce samples into the same growth medium over an extended period of at least one hour or until contamination is detected.

Samples are normally added to a single growth medium for culture. Contemporaneous samples may be introduced into multiple growth media chosen for special selective or diagnostic properties. More than one growth medium would be used whenever more than a single variety of micro-organism is suspected as a possible contaminant and the growth requirements of the two or more suspected varieties of contaminant differ so that a growth medium satisfactory for one is unsatisfactory for another. Many examples of media that may be adapted for these selective applications are described in *The Manual of Clinical Microbiology*, published by the American Society of Microbiology; or the *DIFCO Manual*, published by a media manufacturer. Division of liquid samples is accomplished by means of a suitable division of the outflow of the tubing 19 FIG. 1 into one or more replicates of chamber 21. Normally, a single detection device 27 serves to detect growth in all chambers 21. When the growth of potential varieties of micro-organisms requires provisions of a different gas mixture in chamber 21 to allow growth or organisms that do not grow as well in usual conditions, separate detectors are used in order to avoid mixing the gas mixtures in separate chambers 21.

In the case of a catheterized patient, or in other applications in which it is desirable to detect the presence of any contamination whatsoever, the replaced growth medium should continue to be incubated with a gas detector after replacement for a sufficient length of time for any contamination of the last received sample to be cultured sufficiently to give off gas to be detected by the gas detector. In some applications, it is desirable to detect only the fact that the contamination of the sampled fluid has exceeded a certain minimum level, such as in a city drinking water supply or drinking water from fountains. By controlling the rate at which the growth medium is replaced to be sufficiently high and controlling sensitivity of the radioactive gas detector to be sufficiently low, the radioactive gas detector will provide an indication of the existence of contamination only when the contamination of the sample being introduced into the growth medium exceeds a predetermined minimum level.

Thus, there is provided a system for maintaining substantially continuous monitoring of a fluid to detect incipient contamination thereof much more quickly than was possible with the prior art systems. The above description is of preferred embodiments of the invention and modifications may be made thereto without departing from the spirit and scope of the invention, which is defined in the appended claims.

What is claimed is:

1. A system for continuous monitoring of fluid for microbial contamination comprising container means for containing a growth medium, sampling means in communication with said fluid and operable to aseptically divert said fluid to take periodic samples of said fluid and periodically introduce said samples into said growth medium over an extended period of time, and means for detecting changes that occur in the event of microbial growth in said growth medium during said extended period of time, said sampling means taking said samples automatically at spaced time intervals.

2. An automatic system as recited in claim 1, wherein said sampling means controls the size of said sample to be sufficiently small relative to the volume of the growth medium contained by said container means so that the number of samples introduced into said growth medium during said extended period of time will not substantially affect the characteristics of said growth medium if said samples are uncontaminated.

3. An automatic monitoring system as recited in claim 1, wherein said fluid normally flows through tubing and wherein said sampling means periodically delivers into the growth medium contained by said container a sample of limited volume of the fluid flowing through said tubing.

4. A continuous monitoring system as recited in claim 1, wherein said growth medium is a radio-labeled growth medium, and said means for detecting changes comprises a detector arranged to detect collected radioactive gases evolving from said growth medium.

5. A continuous monitoring system as recited in claim 1, wherein said growth medium is a stable nuclide-labeled growth medium and said means for detecting changes is a detector adopted to detect collected stable nuclide-labeled gases evolving from said growth medium.

6. A continuously monitoring system as recited in claim 1, wherein the time interval between the taking of successive samples by said sampling means is at least ten minutes.

7. A continuous monitoring system as recited in claim 1, wherein there is provided means to maintain the temperature of said growth medium in said container to promote the growth of micro-organisms during said extended time interval.

8. A system for continuous monitoring of fluid for microbial contamination comprising container means for containing a growth medium, sampling means in communication with said fluid and operable to aseptically divert said fluid to take periodic samples of said fluid and periodically introduce said samples into said growth medium over an extended period of time, and means for detecting changes that occur in the event of microbial growth in said growth medium during said extended period of time, said sampling means comprising means to introduce a solid member into a stream of said fluid and then deliver said solid member into said growth medium contained by said container, said solid member being adapted to collect substances from said stream by coming into contact with said fluid in said stream.

9. An apparatus as recited in claim 8, wherein said solid member comprises a strip of material and said sampling means comprises means to incrementally and periodically advance said strip through said stream of fluid and then direct said strip into the growth medium contained in said container.

10. A system for continuous monitoring of fluid for microbial comtamination comprising container means for containing a growth medium, sampling means in communication with said fluid and operable to aseptically divert said fluid to take periodic samples of said fluid and periodically introduce said samples into said growth medium over an extended period of time, and means for detecting changes that occur in the event of microbial growth in said growth medium during said extended period of time, said sampling means comprising means to advance sample discs automatically into a stream of said fluid and then transport the discs into the growth medium contained at said container, said sample disc comprising a material adapted to collect substances from said stream by coming into contact with said stream.

11. A system for continuous monitoring of fluid for microbial contamination comprising container means containing a radio-labeled growth medium having an inlet to receive samples and a gaseous outlet, sampling means in communication with said fluid and connected to said inlet means and operable to aseptically direct said fluid to take periodic samples of said fluid and periodically introduce said samples into said growth medium, a gas permeable membrane obstructing said outlet, temperature control means to control the temperature of said radio-labeled growth medium, agitation means to stir the radio-labeled growth medium, and a nuclide-labeled gas detector connected to said gaseous outlet for detecting radio-labeled gases passing through said membrane.

12. A method of continuously monitoring fluid for the occurrence of microbial contamination comprising providing a growth medium, periodically directing samples of said fluid into said growth medium during an extended time interval whereby successive samples are directed into the same growth medium and detecting changes that occur in said growth medium in association with microbial growth occurs in said growth medium during said extended period of time.

13. A method of monitoring fluid for contamination as recited in claim 12, wherein the volume of said samples are sufficiently small relative to the volume of said growth medium so that the number of samples introduced into said growth medium during said extended time interval will not substantially affect the characteristics of said growth medium if said samples are uncontaminated.

14. A method of monitoring of fluid as recited in claim 12, wherein said growth medium is a radio-labeled growth medium and said step of detecting changes comprises detecting radioactive gases evolving from said growth medium.

15. A method of monitoring fluid as recited in claim 12, wherein said growth medium comprises a stable nuclide-labeled growth medium and said step of detecting changes comprises detecting nuclide-labeled gases evolving from said growth medium.

16. A method of monitoring of fluid as recited in claim 12, further comprising promoting the growth of micro-organisms in said medium during said extended time interval.

17. A method of monitoring fluid as recited in claim 12, wherein said step of periodically directing samples is carried out at spaced time intervals.

18. A method of monitoring fluid as recited in claim 17, wherein the time interval between successive directing of samples of fluid into said medium is at least ten minutes.

19. A method for continuous monitoring of fluid for the occurance of microbial contamination comprising providing a growth medium, periodically at spaced intervals introducing samples into said growth medium wherein successive samples are directed into the same growth medium, and detecting changes that occur in the event of microbial growth in said growth medium, the interval between introducing successive samples into said growth medium being at least 10 minutes.

* * * * *